(12) United States Patent
Watanabe et al.

(10) Patent No.: US 7,267,717 B2
(45) Date of Patent: Sep. 11, 2007

(54) AQUEOUS INK, INK JET RECORDING METHOD, INK CARTRIDGE, RECORDING UNIT, INK JET RECORDING APPARATUS AND IMAGE FORMING METHOD

(75) Inventors: Tomonari Watanabe, Kawasaki (JP); Masashi Ogasawara, Tokyo (JP); Yui Kitamura, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/356,108

(22) Filed: Feb. 17, 2006

(65) Prior Publication Data

US 2006/0132568 A1 Jun. 22, 2006

Related U.S. Application Data

(63) Continuation of application No. PCT/JP2005/016070, filed on Aug. 26, 2005.

(30) Foreign Application Priority Data

Aug. 27, 2004 (JP) .............................. 2004-248228

(51) Int. Cl.
*C09D 11/02* (2006.01)
*G01D 11/00* (2006.01)

(52) U.S. Cl. ..................... 106/31.6; 347/100
(58) Field of Classification Search ............... 106/31.6; 347/100

See application file for complete search history.

(56) References Cited

U.S. PATENT DOCUMENTS

| | | | |
|---|---|---|---|
| 5,609,671 A | 3/1997 | Nagasawa | 106/20 |
| 5,835,116 A | 11/1998 | Sato et al. | 347/98 |
| 6,027,210 A | 2/2000 | Kurabayashi et al. | 347/100 |
| 6,214,100 B1 | 4/2001 | Parazak et al. | 106/31.6 |
| 6,238,045 B1 | 5/2001 | Ono et al. | 347/96 |
| 6,280,513 B1 | 8/2001 | Osumi et al. | 106/31.6 |
| 6,387,168 B1 * | 5/2002 | Koitabashi et al. | 106/31.6 |
| 6,398,355 B1 | 6/2002 | Shirota et al. | 347/100 |

(Continued)

FOREIGN PATENT DOCUMENTS

JP 55-65269 A 5/1980

(Continued)

*Primary Examiner*—J. A Lorengo
*Assistant Examiner*—Veronica Faison-Gee
(74) *Attorney, Agent, or Firm*—Fitzpatrick, Cella, Harper & Scinto

(57) ABSTRACT

An object of the present invention is to provide an aqueous ink which can form a more excellent image in bleeding resistance, character quality and print density than the image formed by using an aqueous ink containing a conventional self-dispersion pigment and a salt. The aqueous ink includes a self-dispersion pigment and a salt, in which the self-dispersion pigment is a pigment containing a pigment particle having a $-R-(COOM_1)_n$ group bonded to a surface of the pigment particle, wherein R represents an alkylene group or an aromatic ring; $M_1$ represents a hydrogen atom, an alkali metal, an ammonium or an organic ammonium; and n is an integer of 2 or more.

21 Claims, 6 Drawing Sheets

U.S. PATENT DOCUMENTS

| | | |
|---|---|---|
| 6,412,936 B1 | 7/2002 | Mafune et al. ............. 347/100 |
| 6,471,757 B1 * | 10/2002 | Koitabashi et al. ...... 106/31.28 |
| 6,521,034 B1 | 2/2003 | Osumi et al. .............. 106/31.6 |
| 6,547,381 B2 | 4/2003 | Watanabe et al. ........... 347/100 |
| 6,572,692 B1 * | 6/2003 | Osumi et al. .............. 106/31.6 |
| 6,706,105 B2 | 3/2004 | Takada et al. .............. 106/31.6 |
| 6,733,120 B2 | 5/2004 | Ogasawara et al. ......... 347/100 |
| 7,005,461 B2 | 2/2006 | Sanada et al. .............. 523/160 |
| 7,160,376 B2 | 1/2007 | Watanabe et al. .......... 106/31.6 |
| 2004/0252170 A1 | 12/2004 | Watanabe et al. .......... 347/100 |
| 2005/0024458 A1 | 2/2005 | Sanada et al. .............. 347/100 |
| 2006/0066699 A1 | 3/2006 | Tokuda et al. .............. 347/100 |
| 2006/0089424 A1 | 4/2006 | Sanada et al. .............. 523/160 |
| 2006/0100311 A1 | 5/2006 | Tokuda et al. .............. 523/160 |

FOREIGN PATENT DOCUMENTS

| | | |
|---|---|---|
| JP | 55-66976 A1 | 5/1980 |
| JP | 63-152681 A | 6/1988 |
| JP | 64-6074 A | 1/1989 |
| JP | 8-3498 | 1/1996 |
| JP | 2000-198955 | 7/2000 |
| JP | 2001-55533 | 2/2001 |
| JP | 2002-80763 | 3/2002 |
| JP | 2004-352981 | 12/2004 |

* cited by examiner

AQUEOUS INK, INK JET RECORDING METHOD, INK CARTRIDGE, RECORDING UNIT, INK JET RECORDING APPARATUS AND IMAGE FORMING METHOD

This application is a continuation of International Application No. PCT/JP2005/016070 filed on Aug. 26, 2005, which claims the benefit of Japanese Patent Application No. 2004-248228 filed on Aug. 27, 2004.

BACKGROUND OF THE INVENTION

1. Field of the Invention

The present invention relates to an aqueous ink, specifically, relates to a recording method and a recording device using an ink jet recording system; further the aqueous ink suitable for an ink jet recording method (an image forming method or a recording method); and an ink jet recording method, an ink cartridge, a recording unit, an ink jet recording apparatus and an image forming method using the aqueous ink.

2. Related Background Art

Up to now, as an ink for a writing implement (a fountain pen, a marking pen and a water-based ball-point pen) and an ink for an ink jet printer, an ink including a pigment which is a colorant capable of providing a recorded matter having high print density and superior fastness has been proposed.

Particularly in resent years, a detailed research has been performed from various viewpoints including the composition and physical properties of the ink, for the purpose of obtaining an adequate document on plain paper such as copying paper, writing paper, a note book, letter paper, bond paper and a continuous business form, which are generally used in an office.

For instance, some patents propose a pigment aqueous ink containing carbon black and a dispersing agent, as a pigment ink having the above described property (see Japanese Patent Application Laid-Open No. S61-283875 and Japanese Patent Application Laid-Open No. S64-6074 for instance).

Another patent points out a technical problem that when an ink containing carbon black as pigment and containing a dispersing agent is used for an ink in an ink jet recording apparatus, the ink is unstably ejected and adequate print density is not obtained, and proposes a pigment aqueous ink containing so called self-dispersion carbon black which can be dispersed without using a dispersing agent, as an ink for solving such a problem (see Japanese Patent Application Laid-Open. No. H8-3498 for instance).

When using the above described pigment aqueous ink as a black ink, and recording a color image in combination with other color inks (for instance, at least one ink selected from a magenta ink, a cyan ink, a yellow ink, a red ink, a green ink and a blue ink), a problem described below occurs. Specifically, such a phenomenon as boundary between a black image and a color image formed on a recording medium smears, or the inks are non-uniformly mixed to deteriorate image quality (hereafter called "bleeding") occurs. Other patents propose a method for improving the permeability of ink to a recording medium by adding a surfactant to the ink, as means for inhibiting the bleeding, in other words, for improving bleeding resistance (see Japanese Patent Application Laid-Open No. S55-65269 for instance), or a method for improving a drying rate of the ink applied to the recording medium, by mainly using a volatile solvent for the solvent of the ink (see Japanese Patent Application Laid-Open No. S55-66976 for instance). Furthermore, other patents propose a method for improving not only bleeding resistance but also character quality and print density, by using a black ink containing a self-dispersion carbon black and a particular salt (see Japanese Patent Application Laid-Open No. 2000-198955 and Japanese Patent Application Laid-Open No. 2002-80763, for instance).

SUMMARY OF THE INVENTION

By using aqueous ink containing self-dispersion carbon black and a salt as described above, image characteristics such as bleeding resistance, character quality and print density have already reached a level having no problem.

The present inventors researched phenomena occurring on a recording medium in detail, for the purpose of providing an image with further superior quality. As a result, it was found that a type and a structure of a surface functional group of a self-dispersion pigment greatly contributes to improvement in the above described image quality. A self-dispersion pigment contained in the ink applied onto the recording medium becomes unstably dispersed and aggregates with each other, due to the vaporization and diffusion of moisture and the variation of a content ratio in the ink. It was found that when the phenomenon is going to occur, the self-dispersion pigment having a particular type and structure of a surface functional group thereon can show greatly improved image characteristics such as bleeding resistance, character quality and print density compared to image characteristics obtained by using the aqueous ink containing the conventional self-dispersion pigment and a salt.

As a result of research by the present inventors, it was found that the ink which contains the self-dispersion pigment having a particular type and structure of the surface functional group as described above, and which further contains adequately selected type of a salt to be used together with the self-dispersion pigment, shows superior characteristics such as water resistance and dispersion stability when moisture has vaporized.

Accordingly, an object of the present invention is to provide an aqueous ink which can form a more excellent image in bleeding resistance, character quality and print density than the image formed by using an aqueous ink containing conventional self-dispersion pigment and a salt.

Another object of the present invention is to provide an aqueous ink which can form an image with adequate water resistance in addition to the above described effect.

Another object of the present invention is to provide aqueous ink having adequate ink characteristics such as dispersion stability when moisture has vaporized in addition to the above described effects.

Another object of the present invention is to provide an ink jet recording method, an ink cartridge, a recording unit and an ink jet recording apparatus, each of which uses the aqueous ink with the above described composition.

Another object of the present invention is to provide an image forming method that can effectively inhibit color mixture (bleeding) from occurring on a boundary of regions of the black and color inks, when a color image having the regions of different colors each other adjacent is recorded on a plain paper.

The above described object is achieved by the present invention described below. That is, an aqueous ink according to the present invention comprises a self-dispersion pigment and a salt, wherein the self-dispersion pigment is a pigment containing a pigment particle having a —R—$(COOM_1)_n$ group bonded to a surface of the pigment particle, wherein R represents an alkylene group or an aromatic ring; $M_1$ represents a hydrogen atom, an alkali metal, an ammonium or an organic ammonium; and n is an integer of 2 or larger.

An ink jet recording method according to another aspect according to the present invention comprises a step of ejecting an ink by an ink jet method, wherein the ink is the above described composition.

An ink cartridge according to another aspect according to the present invention comprises an ink containing portion for containing an ink, wherein the ink is the above described composition.

A recording unit according to another aspect according to the present invention comprises an ink containing portion for containing an ink and a recording head for ejecting an ink therefrom, wherein the ink is the above described composition.

An ink jet recording apparatus according to another aspect according to the present invention comprises an ink containing portion for containing an ink and a recording head for ejecting an ink therefrom, wherein the ink is the above described composition.

An image forming method for performing recording on plain paper by an ink jet recording method by using a black ink and at least one color ink, according to another aspect according to the present invention wherein the aqueous ink having the above described composition is used as black ink, and wherein in forming an image composed of an image formed by the black ink and an image formed by the color ink are adjacent to each other, performing scanning for applying the black to form the image and thereafter performing scanning for applying the color ink to the area where the image has been formed by the precedent scanning.

An aqueous ink according to another aspect according to the present invention comprises a self-dispersion pigment and $M_1^+$, wherein the self-dispersion pigment is a pigment containing a pigment particle having a —R—(COO$^-$)$_n$ group bonded to a surface of the pigment particle, wherein, R represents an alkylene group or an aromatic ring; and n is an integer of 2 or larger, and wherein $M_1$ represents a hydrogen atom, an alkali metal, an ammonium or an organic ammonium, and wherein the aqueous ink further comprises at least one group selected from the group consisting of $NO_3^-$, $CH_3COO^-$, $C_6H_5COO^-$, $C_2H_4(COO^-)_2$, $C_6H_4(COO^-)_2$ and $SO_4^{2-}$ and $M_2^+$, wherein, $M_2$ represents an alkali metal, an ammonium or an organic ammonium.

The present invention can provide an aqueous ink which can form a more excellent image in bleeding resistance, character quality and print density than the image formed by using an aqueous ink containing conventional self-dispersion pigment and a salt. Another aspect according to the present invention can provide an aqueous ink which can form an image with adequate water resistance in addition to the above described effect. Another aspect according to the present invention can provide an aqueous ink having adequate ink characteristics such as dispersion stability when moisture has vaporized in addition to the above described effects. Another aspect according to the present invention can provide an ink jet recording method, an ink cartridge, a recording unit and an ink jet recording apparatus, each of which uses the aqueous ink with the above described composition. Another aspect according to the present invention can provide an image forming method that can effectively inhibit color mixture (bleeding) from occurring on a boundary of each color image, when a color image having the regions of different colors each other adjacent is recorded on a plain paper.

DESCRIPTION OF THE PREFERRED EMBODIMENTS

Figure 1:
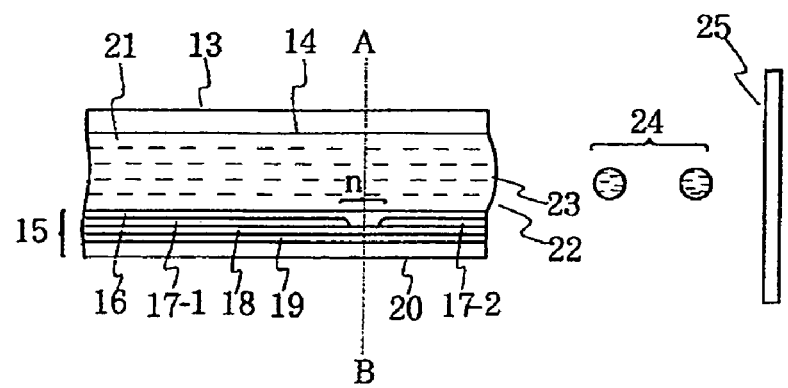
FIG. 1 is a cross sectional view in a longitudinal direction of a head of an ink jet recording apparatus.

The present invention will be further described in detail below by showing the best mode for carrying out the invention.

An aqueous ink according to the present invention includes using a self-dispersion pigment containing a pigment particle having a —R—(COOM$_1$)$_n$ group, (wherein, R represents an alkylene group or an aromatic ring; $M_1$ represents a hydrogen atom, an alkali metal, an ammonium or an organic ammonium; and n is an integer of 2 or larger) bonded to a surface of the pigment particle, as a coloring material; and further includes a salt.

A leading reason is assumed to be an interaction between the self-dispersion pigment and a water-soluble organic solvent in the ink, why an aqueous ink using a self-dispersion pigment containing a pigment particle having a —R—(COOM$_1$)$_n$ group bonded to a surface of the pigment particle shows greatly improved image characteristics such as bleeding resistance, character quality and print density compared to image characteristics obtained by using the aqueous ink containing the conventional self-dispersion pigment as the coloring material. Specifically, it is considered that when the self-dispersion pigment having the —R—(COOM$_1$)$_n$ group bonded to the surface of the pigment particle is used as the coloring material, and particularly, when the above described —R—(COOM$_1$)$_n$ group is bonded to the surface of the pigment particle into high density, a phenomenon described below occurs.

A pigment particle having a —R—(COOM$_1$)$_n$ group bonded to its surface is difficult to be solvated with a water-soluble organic solvent existing around it in the ink, compared to a combination of a conventional self-dispersion pigment and the water-soluble organic solvent existing around it, because the —R—(COOM$_1$)$_n$ group may cause a greater steric hindrance. It is considered that as a result of this, when the ink has been applied to a recording medium, a solid content including the pigment extremely promptly causes the separation from the water-soluble organic solvent (solid-liquid separation) in the ink. It is also considered that when the pigment is difficult to be solvated with the water-soluble organic solvent contained in the ink, the pigment has a less stable dispersion due to a smaller solvation effect in the ink, and the pigment particles aggregate to a greater extent on the recording medium.

Furthermore, the present inventors have conducted various studies on a counter ion for the self-dispersion pigment having the —R—$(COOM_1)_n$ group bonded to the surface of the pigment particle and the salt made to be contained in the ink in combination with the above described self-dispersion pigment. As a result, it was found that when the above described self-dispersion pigment is combined with a particular salt among the above described salts, the particular combination can improve not only a superior effect of improving bleeding resistance, character quality and print density, as was described above, but also ink characteristics such as water resistance and dispersion stability when moisture vaporizes. The reason why the above described effect is obtained by the combination of the particular self-dispersion pigment with the particular salt is not clear, but it is assumed to be associated with the molecular structure, dissociation equilibrium constant and solubility of a functional group bonded to the pigment surface and a salt.

By the way, salvation in the present invention means the affinity of pigment with a water-soluble organic solvent, and the affinity depends on how many sites having the affinity to the water-soluble organic solvent the pigment has. The site having the affinity to the water-soluble organic solvent includes, for instance, a site having no ionic group bonded to the surface of a pigment particle. For instance, when the group having ionicity is bonded to the surface of the pigment particle in high density, the area in which the sites having the affinity to the water-soluble organic solvent are exposed is small in the surface area of the pigment particle. It is also assumed that when the ionic group covers the pigment particle surface at a higher density, the pigment becomes difficult to be solvated with the water-soluble organic solvent due to a synergistic effect of the influence of steric hindrance by the ionic group and the influence of reduced sites having the affinity to the water-soluble organic solvent of the pigment.

(Aqueous Ink)

A self-dispersion pigment, salt, an aqueous medium and other contents composing aqueous ink according to the present invention will be now described below.

(Self-dispersion Pigment)

A coloring material used in an aqueous ink according to the present invention is a self-dispersion pigment containing a pigment particle having a —R—$(COOM_1)_n$ group bonded to a surface of the pigment particle, wherein R represents an alkylene group or an aromatic ring; $M_1$ represents a hydrogen atom, an alkali metal, an ammonium or an organic ammonium; and n is an integer of 2 or larger. A state of the —R—$(COOM_1)_n$ group in the ink may be any of the states in which one part of the groups is dissociated, and in which all the groups are dissociated.

Among them, a pigment having a compound having a structure of the above described —R—$(COOM_1)_n$ group in a part bonded to the surface, which is obtained with a diazo coupling method, can be preferably used. As a matter of course, the present invention is not limited to the pigment. These self-dispersion pigments can be not only singly used but also be used in combinations of two or more pigments.

Here, the alkylene group according to the present invention includes, for instance, a methylene group, an ethylene group and a propylene group. The aromatic ring according to the present invention includes, for instance, a benzene ring and a naphthalene ring. As a matter of course, the present invention is not limited to the groups.

A more preferable aspect for more remarkably developing the effect of the present invention is the case in which a carbon atom adjacent to a carbon atom bound to —$(COOM_1)$, in —R— bonded to the surface of the pigment particle, is also bound to —$(COOM_1)$, the case in which the n is 2, or the case in which the R is $C_6H_3$. In the above description, the case in which the carbon atom adjacent to the carbon atom bound to —$(COOM_1)$ in —R— bonded to the surface of the above described pigment particle is also bound to —$(COOM_1)$ means the case in which all of two or more adjacent carbon atoms in R have the —$(COOM_1)$ group, as is described in the following structural formula (1). In the present invention, it is preferable to use a self-dispersion pigment having a group shown in the following structural formula (1), bonded to the surface of the pigment particle. As a matter of course, the present invention is not limited to the self-dispersion pigment.

Structural Formula (I)

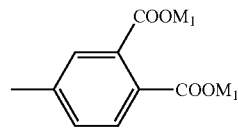

In addition, in the aqueous ink according to the present invention, the pigment particle having the above —R—$(COOM_1)_n$ group bonded to its surface at a higher density, for example, at a density of ionic groups of 2.00 µmol/m² or more on the pigment particle surface, is particularly preferable because the aqueous ink further promotes solid-liquid separation of the pigment caused by a low level of the above described salvation, and more remarkably provides the effect of the present invention. However, in the present invention, the density of the ionic group on the pigment particle surface is greatly affected by a specific surface area of the pigment and a structure of the functional group bonded to the pigment particle surface, so that the density is not limited to the above described range.

Furthermore, the above described $M_1$ in an aqueous ink according to the present invention is particularly preferably ammonium because of providing further superior water resistance. The reason is considered to be because when the ink is applied to a recording medium, the ammonium decomposes into vapor and the ionic group bonded to the surface of carbon black is converted to a H type (an acid type), which lowers the hydrophilicity of the pigment. Here, self-dispersion carbon black having $M_1$ of ammonium can be obtained by a method described below. The method includes, for instance, the method of using the self-dispersion carbon black having the $M_1$ of an alkali metal and substituting ammonium for the $M_1$ with an ion exchange method; and the method of adding acid to the same self-dispersion carbon black to convert the functional group into an H type, and adding ammonium hydroxide to it to convert the $M_1$ into ammonium.

(Pigment Particle)

A pigment particle that can be used in aqueous ink according to the present invention is not particularly limited, and any pigment particle shown below can be used. When the aqueous ink according to the present invention is used as black ink, it is preferable to use carbon black as the pigment particle.

A specific example of carbon black includes, for instance, furnace black, lamp black, acetylene black and channel black. More specific usable commercial products are, for instance, Raven 7000, Raven 5750, Raven 5250, Raven 5000ULTRA, Raven 3500, Raven 2000, Raven 1500, Raven 1250, Raven 1200, Raven 1190ULTRA-II, Raven 1170 and Raven 1255 (up to this point, made by Colombia); Black Pearls L, Regal 400R, Regal 330R, Regal 660R, Mogul L, Monarch 700, Monarch, 800, Monarch 880, Monarch 900, Monarch 1,000, Monarch 1,100, Monarch 1,300, Monarch 1,400, Monarch 2,000 and Vulcan XC-72R (up to this point, made by Cabot Corporation); Color Black FW1, Color Black FW2, Color Black FW2V, Color Black FW18, Color Black; FW200, Color Black S150, Color Black S160, Color Black S170, Printex 35, Printex U, Printex V, Printex 140U, Printex 140V, Special Black 6, Special Black 5, Special Black 4A and Special Black 4 (up to this point, made by Degussa Ltd.); and No. 25, No. 33, No. 40, No. 47, No. 52, No. 900, No. 2300, MCF-88, MA600, MA7, MA8 and MA100 (up to this point, made by Mitsubishi Chemical Corporation). In addition, the carbon black separately newly prepared for the present invention can be used. However, the present invention is not limited by the pigment particles, abut any conventionally well-known carbon black can be used. In addition, a black pigment is not limited to the carbon black, but may employ a particle of a magnetic substance such as magnetite and ferrite, titanium black or the like.

A usable pigment particle other than black ink includes various organic pigment particles. Specifically, the organic pigment particle includes, for instance, insoluble azo pigments such as Toluidine Red, Toluidine maroon, Hanza Yellow, Benzidine Yellow and Pyrazolone Red; soluble azo pigments such as Lithol Red, Helio Bordeaux, Pigment Scarlet and Permanent Red 2B; derivatives from vat dyes, such as alizarin, indanthrone and Thioindigo maroon; phtalocyanine-based pigment such as Phthalocyanine Blue and Phthalocyanine Green; quinacridone type pigments such as Quinacridone Red and Quinacridone Magenta; perylene type pigments such as Perylene Red and Perylene Scarlet; isoindolinone type pigments such as Isoindolinone Yellow and Isoindolinone Orange; imidazolone type pigments such as Benzimidazolone Yellow, Benzimidazolone Orange and Benzimidazolone Red; pyranthrone type pigments such as Pyranthrone Red and Pyranthrone Orange; and indigo type pigments, condensation azo type pigments, thioindigo type pigments, diketopyrrolopyrrole type pigments, Flavanthrone Yellow, Acyl Amide Yellow, Quinophthalone Yellow, Nickel Azo Yellow, Copper Azomethine Yellow, Perinone Orange, Anthrone Orange, Dianthraquinonyl Red, and Dioxazine Violet. As a matter of course, the organic pigment is not limited to those, but other organic pigments may be used.

In addition, when usable organic pigments in the present invention are shown by the Colour index number, they include the followings:

C. I. pigment yellow: 12, 13, 14, 17, 20, 24, 74, 83, 86, 93, 97, 109, 110, 117, 120, 125, 128, 137, 138, 147, 148, 150, 151, 153, 154, 166, 168, 180, 185 and the like;

C. I. pigment orange: 16, 36, 43, 51, 55, 59, 61, 71 and the like;

C. I. pigment red: 9, 48, 49, 52, 53, 57, 97, 122, 123, 149, 168, 175, 176, 177, 180, 192, 215, 216, 217, 220, 223, 224, 226, 227, 228, 238, 240, 254, 255, 272 and the like;

C. I. pigment violet 19, 23, 29, 30, 37, 40, 50 and the like;

C. I. pigment blue: 15, 15:1, 15:3, 15:4, 15:6, 22, 60, 64 and the like;

C. I. pigment green: 7, 36 and the like; and

C. I. pigment brown: 23, 25, 26 and the like.

The content (mass %) of pigment in an aqueous ink according to the present invention is preferably 0.1 to 15 mass % with respect to the total mass of the ink, and particularly preferably is 1 to 10 mass %.

(Salt)

It is essential for aqueous ink according to the present invention to contain a salt. The state of the salt in the ink may be any of the states in which one part of the salt is dissociated, and in which the salt is completely dissociated.

A specific example of a salt which can be used in an aqueous ink according to the present invention includes, for instance, $(M_2)NO_3$, $CH_3COO(M_2)$, $C_6H_5COO(M_2)$, $C_2H_4(COO(M_2))_2$, $C_6H_4(COO(M_2))_2$ and $(M_2)_2SO_4$ (wherein, $M_2$ represents an alkali metal, an ammonium or an organic ammonium). As a matter of course, the invention is not limited by the examples as far as it satisfies the requirements according to the present invention.

The salt has only to be contained in an aqueous ink according to the present invention in such a range as to sufficiently obtain an effect of the present invention. Specifically, the content (mass %) of the salt is preferably 0.05 to 10.0 mass % with respect to the total mass of the ink. When the content of the salt is less than 0.05 mass %, the aqueous ink may not provide the effect of the present invention, when the content of the salt is more than 10.0 mass %, the aqueous ink may not provide an adequate storage stability of the ink.

In addition, the aqueous ink according to the present invention more preferably has ammonium for the above described $M_2$ in order to provide superior water resistance. Among them, salts particularly preferable are $NH_4NO_3$, $C_2H_4(COONH_4)_2$, $C_6H_4(COONH_4)_2$ and $(NH_4)_2SO_4$, because the ink develops water resistance in a comparatively short time.

The salt in the aqueous ink according to the present invention is more preferably $C_2H_4(COO(M_2))_2$, $C_6H_4(COO(M_2))_2$ and $(M_2)_2SO_4$, because it gives a pigment particularly superior dispersion stability when moisture included in the ink has vaporized.

In addition, it is particularly preferable that the aqueous ink contains a salt having an equal valency to that of a functional group on the surface of the particle of a self-dispersion pigment containing a pigment particle having a —R—$(COOM_1)_n$ group bonded to a surface of the pigment particle. As a salt to be used in combination with the self-dispersion pigment, specifically for instance, that when the n is 2, the aqueous ink contains a salt having the valency of two to be used in combination with the self-dispersion pigment is particularly preferable, because such an aqueous ink remarkably shows effects of the present invention. The specific combination includes the combination of the self-dispersion pigment having the —R—$(COOM_1)_2$ group bonded to the pigment particle surface, and one or more salts selected among $C_2H_4(COO(M_2))_2$, $C_6H_4(COO(M_2))_2$ and $(M_2)_2SO_4$. As a matter of course, the present invention is not limited to the combinations.

(Aqueous Medium)

An aqueous medium used in the aqueous ink according to the present invention is water alone, or a mixed solvent of water and a water-soluble organic solvent. The above described water-soluble organic solvent has particularly preferably the effect of preventing the drying of ink. The water is preferably not a common water containing various ions but deionized water.

Specifically, a water-soluble organic solvent includes, for instance, an alkyl alcohol having 1 to 4 carbon atoms such as methyl alcohol, ethyl alcohol, n-propyl alcohol, isopropyl alcohol, n-butyl alcohol, sec-butyl alcohol and tert-butyl alcohol; an amide such as dimethylformamide and dimethylacetamide; a ketone or a keto-alcohol such as acetone and diacetone alcohol; an ether such as tetrahydrofuran and dioxane; a polyalkylene glycol such as polyethylene glycol and polypropylene glycol; an alkyleneglycol with an alkylene group having 2 to 6 carbon atoms such as ethyleneglycol, propyleneglycol, butyleneglycol, triethyleneglycol, 1,2,6-hexane triol, thiodiglycol, hexyleneglycol and diethyleneglycol; a lower alkyletheracetate such as polyethyleneglycolmonomethylether acetate; glycerin; a low-grade alkyl ether of a polyhydric alcohol, such as ethyleneglycol monomethyl (or ethyl) ether, diethyleneglycol methyl (or ethyl) ether and triethyleneglycol monomethyl (or ethyl) ether; and N-methyl-2-pyrrolidone, 2-pyrrolidone and 1,3-dimethyl-2-imidazolidinone. The above described water-soluble organic solvent may be used singly or in the form of a mixture.

The content of the water-soluble organic solvent in the aqueous ink according to the present invention is not limited in particular, but is preferably 3 mass % or more and 50 mass % or less with respect to the total mass of the ink. In addition, the content of the water in the aqueous ink is preferably 50 mass % or more and 95 mass % or less with respect to the total mass of the ink.

(Other Components)

An aqueous ink according to the present invention may employ a moisture retentive component such as urea, a urea derivative, trimethylolpropane and trimethylolethane for retaining moisture as an ink component, in addition to the above described components. The content of the moisture retentive component such as urea, a urea derivative and trimethylolpropane is preferably 0.1 to 20.0 mass % with respect to the total mass of the ink in general, and more preferably is 3.0 to 10.0 mass %.

Furthermore, the aqueous ink according to the present invention may contain various additives such as a surfactant, a pH moderator, an antifoaming agent, a rust inhibitor, an antiseptic agent, a mildew-proofing agent, an antioxidant, a reduction inhibitor, an evaporation accelerator and, a chelating agent in addition to the above described component as needed, in order to apply the ink desirable physical properties; and can further contain a commercially-available water-soluble dye.

When the aqueous ink is needed to have its surface tension adjusted, it is effective to optionally add a surfactant such as an acetylene alcohol shown in the following structural formula (2) or a penetrating solvent to the ink.

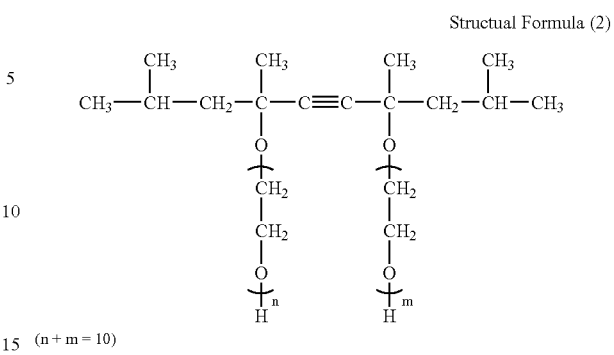

Structual Formula (2)

$(n+m=10)$

The addition of a polymer or the like to the ink as needed, also can improve resistance to rubbing and resistance to highlighter pens. Among the polymers, a nonionic polymer having no ionic group seldom affects the reliability of the ink, and accordingly can be preferably used.

(Color Ink)

The inventive image forming method comprises the image forming method for performing recording on plain paper by an ink jet recording method by using a black ink and at least one color ink, wherein the black ink is an aqueous ink having the above described composition, and wherein in forming an image composed of an image formed by the black ink and an image formed by the color ink are adjacent to each other, performing scanning for applying the black to form the image and thereafter performing scanning for applying the color ink to the area where the image has been formed by the precedent scanning. Color inks will be now described each of which can be used when the inventive aqueous ink is applied only to the black ink. In the inventive image forming method any known conventional color ink for ink jet recording is suitable.

A coloring material for the color ink includes a water-soluble dye, and the water-soluble dye particularly preferably has an anionic group as a soluble group. The color of the color ink to be used in the present invention can be appropriately selected from, for instance, cyan, magenta, yellow, red, green, blue and orange.

The water-soluble dye having the anionic group to be used in the present invention is not particularly limited as long as it is a water-soluble acid dye, direct dye and reactive dye described in the Colour index. A dye which is not described in the Colour index can also be used. Particularly, a preferably used water-soluble dye has an anionic group, for instance, a sulfonic group. The usable content of these dyes in ink is in the range of 1 to 10 mass %, and preferably of 1 to 5 mass %.

The specific dye includes the followings:

C. I. direct yellow: 8, 11, 12, 27, 28, 33, 39, 44, 50, 58, 85, 86, 87, 88, 98, 100, 110 and the like;

C. I. direct red: 2, 4, 9, 11, 20, 23, 24, 31, 39, 46, 62, 75, 79, 80, 83, 89, 95, 197, 201, 218, 220, 224, 225, 226, 227, 228, 230 and the like;

C. I. direct blue: 1, 15, 22, 25, 41, 76, 77, 80, 86, 90, 98, 106, 108, 120, 158, 163, 168, 199, 226 and the like;

C. I. acid yellow: 1, 3, 7, 11, 17, 23, 25, 29, 36, 38, 40, 42, 44, 76, 98, 99 and the like;

C. I. acid red: 6, 8, 9, 13, 14, 18, 26, 27, 32, 35, 42, 51, 52, 80, 83, 87, 89, 92, 94, 106, 114, 115, 133, 134, 145, 158, 198, 249, 265, 289 and the like; and C. I. acid blue: 1, 7, 9, 15, 22, 23, 25, 29, 40, 43, 59, 62, 74, 78, 80, 90, 100, 102, 104, 117, 127, 138, 158, 161 and the like.

In addition to the above described water-soluble dye, a coloring material for a color ink can include the following substances 1 to 3. These coloring materials are preferable because many of them show superior water resistance after having been applied onto a recording medium.

1. Dye having a carboxyl group for a soluble group
2. Oil-soluble dye
3. Pigment An oil-soluble dye is not limited in particular as long as it is described in the Colour index. In addition, the oil-soluble dye is not limited in particular, even though it is a new dye which is not described in the Colour index. Specifically, the dyes are described below. The content of the dyes in the ink is preferably in a range of 1 to 10 mass %, and further preferably of 1 to 5 mass %.

C. I. solvent yellow: 1, 49, 62, 74, 79, 82, 83, 89, 90, 120, 121, 151, 153, 154 and the like C. I. solvent red: 25, 31, 86, 92, 97, 118, 132, 160, 186, 187, 219 and the like C. I. solvent blue: 33, 38, 42, 45, 53, 65, 67, 70, 104, 114, 115, 135 and the like When pigment is used as a coloring material of color ink, the content of the pigment is preferably 1 to 20 mass % with respect to the total mass of the ink, and further preferably is 2 to 12 mass %. The pigments that can be used in the present invention are described below. As a matter of course, the present invention is not limited to the pigments. As a matter of course, the pigment newly produced for the present invention can also be used.

C. I. pigment yellow: 1, 2, 3, 13, 16, 74, 83, 128 and the like

C. I. pigment red: 5, 7, 12, 48 (Ca), 48 (Mn), 57 (Ca), 112, 122 and the like

C. I. pigment blue: 1, 2, 3, 15:3, 16, 22 and the like

C. I. vat blue: 4, 6 and the like

A dispersing agent which is used for dispersing the pigment into the ink, when a pigment is used as a coloring material of a color ink, is not particularly limited as long as it is a water-soluble resin, but has preferably a weight average molecular weight in a range of 1,000 to 30,000, and further preferably of 3,000 to 15,000. The dispersing agent specifically includes a block copolymer, a random copolymer, a graft copolymer or a salt thereof, each consisting of at least two monomers (at least one of them being a hydrophilic monomer) selected among styrene, a styrene derivative, vinylnaphthalene, a vinylnaphthalene derivative, an aliphatic alcohol ester of an $\alpha,\beta$-ethylenic unsaturated carboxylic acid, acrylic acid, an acrylic acid derivative, maleic acid, a maleic acid derivative, itaconic acid, an itaconic acid derivative, fumaric acid, a fumaric acid derivative, and vinyl acetate, vinylpyrrolidone, acrylamide and derivatives thereof. A natural resin such as rosin, shellac and starch can also be preferably used. These resins can be dissolved in an aqueous solution containing a base-dissolved therein, and are alkali-soluble resins. The content of the above described water-soluble resins to be used as a dispersing agent is preferably in a range of 0.1 to 5 mass % with respect to the total mass of the ink.

The aqueous medium used in color ink is water, or a mixed solvent of water and a water-soluble organic solvent. The water is preferably not a common water containing various ions but deionized water.

Specific examples of the water-soluble organic solvent includes, for instance, an alkyl alcohol having 1 to 4 carbon atoms such as methyl alcohol, ethyl alcohol, n-propyl alcohol, isopropyl alcohol, n-butyl alcohol, sec-butyl alcohol and tert-butyl alcohol; an amide such as dimethylformamide and dimethylacetamide; a ketone or a keto-alcohol such as acetone and diacetone alcohol; an ether such as tetrahydrofuran and dioxane; a polyalkylene glycol such as polyethylene glycol and polypropylene glycol; an alkyleneglycol with an alkylene group having 2 to 6 carbon atoms such as ethyleneglycol, propyleneglycol, butyleneglycol, triethyleneglycol, 1,2,6-hexane triol, thiodiglycol, hexyleneglycol and diethyleneglycol; glycerin; a low-grade alkyl ether of a polyhydric alcohol, such as ethyleneglycol monomethyl (or ethyl) ether, diethyleneglycol methyl (or ethyl) ether and triethyleneglycol monomethyl (or ethyl) ether; and N-methyl-2-pyrrolidone, 2-pyrrolidone and 1,3-dimethyl-2-imidazolidinone. Among these water-soluble organic solvents, a polyhydric alcohol such as diethyleneglycol, and a low-grade alkyl ether of a polyhydric alcohol such as triethyleneglycol monomethyl (or ethyl) ether are particularly preferable.

The content of the water-soluble organic solvent in the color ink is preferably in a range of 3 to 50 mass % with respect to the total mass of the ink, and further preferably of 3 to 40 mass %. In addition, the content of water in the color ink is preferably in a range of 10 to 90 mass %, and further preferably of 30 to 80 mass %.

A color ink used in the present invention can appropriately contain a surfactant, an antifoaming agent and an antiseptic agent in addition to the above described component as needed, in order to apply the ink desirable physical properties.

(Physical Property of Ink)

Black and color inks having the above described compositions to be used in the present invention have preferably such characteristics as to be adequately ejected from an ink jet recording head. From a viewpoint of the ejectability of the ink from the ink jet recording head, the ink preferably has characteristics, for instance, a viscosity of 1 to 15 mPa·s and a surface tension of 25 mN/m or larger, and further preferably a viscosity of 1 to 5 mPa·s and a surface tension of 25 to 50 mN/m. In addition, when the black ink and the color ink are concomitantly used, the color ink has preferably a lower surface tension than that the black ink has. Specifically, it is preferable that the black ink has a surface tension of 35 to 50 mN/m, and the color ink has a surface tension of 25 to 35 mN/m.

As for a measure for expressing the permeability of ink into a recording medium, there is a Ka value determined by the Bristow method. Specifically, when the permeability of the ink is expressed by an ink amount V per square meter, an amount V (ml/m$^2$=$\mu$m) of the ink which has permeated into the recording medium in a period of time after the ink has been ejected as an ink drop and before a predetermined time t elapses is shown by the Bristow Equation (equation (1)) described below.

$$V = Vr + Ka(t-tw)^{1/2} \qquad \text{equation (1)}$$

Most of the ink is absorbed in an uneven portion on the surface of a recording medium (a rough part of the surface of the recording medium), right after it has been applied onto the recording medium, but the ink permeates only slightly into the recording medium (in a depth direction). The period of time is a contacting period of time (tw), and Vr is the amount of the ink absorbed in the uneven portion of the recording medium during the contacting period of time.

When the period of time after the ink has been applied onto the recording medium exceeds the contacting period of time, the ink starts permeation into the recording medium (in a depth direction), and the amount of the permeated ink increases in proportion a ½ power of the period of time after the contacting period of time, or equivalently, of (t−tw). Ka is the proportionality coefficient of an increment, and takes a value corresponding to a permeation rate. By the way, the Ka value can be measured with a device using the Bristow method for testing the dynamic permeability of a liquid (for instance, trade name: Dynamic Permeability Tester S; made by Toyo Seiki Manufacturing Co.).

According to further research carried out by the present inventors, from a viewpoint of further improving the quality of the formed recorded image, the Ka value in the ink is preferably adjusted to less than 1.5 (ml/m$^2$/msec$^{1/2}$), and further preferably adjusted to 0.2 (ml/m$^2$/msec$^{1/2}$) or more and less than 1.5 (ml/m$^2$/msec$^{1/2}$) Specifically, when the ink is composed so as to have the Ka value less than 1.5 (ml/m$^2$/msec$^{1/2}$), the ink causes solid-liquid separation in an early stage of a penetrating process of the ink into the recording medium, and can form the image of high quality.

Here, a Ka value by the Bristow method in the present invention is a value measured by using plain paper (for instance, PB paper for a copying machine using an electrophotographic system, a page printer (a laser beam printer) and a printer using an ink jet recording system, made by Canon Inc., or PPC paper for the copying machine using the electrophotographic system), as a recording medium. The measurement was carried out in an environment that is assumed to be a general office environment, for instance, at a temperature of 20 to 25° C. and a humidity of 40 to 60%.

In order to provide an ink with the above described physical properties, it is particularly preferable that the inventive aqueous ink contains, for instance, glycerin, trimethylolpropane, thiodiglycol, ethyleneglycol, diethyleneglycol, isopropyl alcohol or acetylene alcohol, as the water-soluble organic solvent.

(Image Forming Method)

In the paragraphs that follow, an image forming method according to the present invention will be described with reference to specific examples. The inventive image forming method comprises the image forming method for performing recording on plain paper by an ink jet recording method by using a black ink and at least one color ink, wherein the black ink is an aqueous ink having the above described composition, and wherein in forming an image composed of an image formed by the black ink and an image formed by the color ink are adjacent to each other, performing scanning for applying the black to form the image and thereafter performing scanning for applying the color ink to the area where the image has been formed by the precedent scanning. The image forming method according to the present invention will be now described in detail below.

Figure 8:
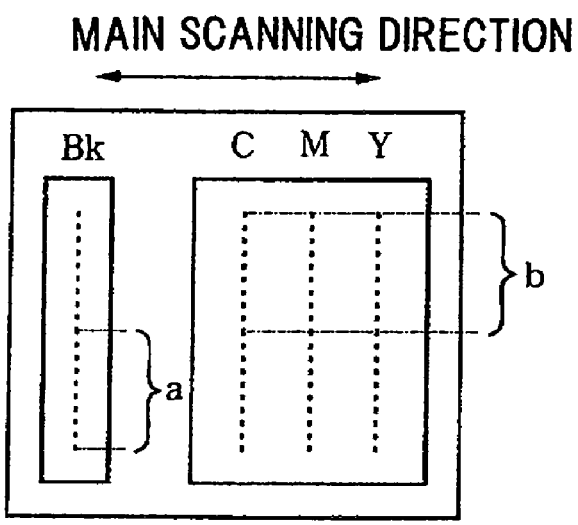
FIG. 8 is a view showing an example of a recording head used in the present invention.

FIG. 8 shows an example of a recording head that is used in carrying out the image forming method according to the present invention. The recording head, as shown in FIG. 8, is provided with an ejection orifice line (Bk) for ejecting black ink, and an ejection orifice line for ejecting each of three color inks of cyan (C), magenta (M) and yellow (Y).

The image forming method according to the present invention, when forming the full-color image, preferably employs a recording head having such an ejection orifice line for ejecting black ink and an ejection orifice line for ejecting a color ink as are placed to be shifted from each other in the sub-scanning direction. Specifically, when forming an image with the use of a recording head shown in FIG. 8 for instance, it is preferable to use the whole region of an ejection orifice line for black ink when forming the image of only a black color, and to use a part a of the ejection orifice line for black ink, for the black ink, and a part b of the ejection orifice line for color ink, for the color inks C, M and Y, when forming a full-color image in which an image of the black and an image of colors are mixed. A method of forming the image in which the image of the black and the image of colors are mixed will be described further in detail below.

FIG. 8 shows one example of a recording head that can be used in the present invention. The recording head is provided with an ejection orifice line (Bk) for ejecting a black ink, and an ejection orifice line for ejecting each of three-color inks of cyan (C), magenta (M) and yellow (Y). At first, an image of black is formed on a recording medium by one-pass recording, by scanning the recording head in a transverse direction (a main-scanning direction) of the figure, with the use of a part a of the ejection orifice line for the black ink. Subsequently, the recording medium is carried by a distance only a in a longitudinal direction (a sub-scanning direction) of the figure, and while the recording head is moving in a forward scanning direction, the recording head forms the color image in a image region which has been previously formed by using the part a of the ejection orifice line for the black ink on the recording medium by one-pass recording, with the use of a part b of the ejection orifice line for the color ink. At this time, the part a of the ejection orifice line for the black ink forms the image in the next region. By this repetition, the image having the black image and the color image mixed therein is formed.

Figure 9:
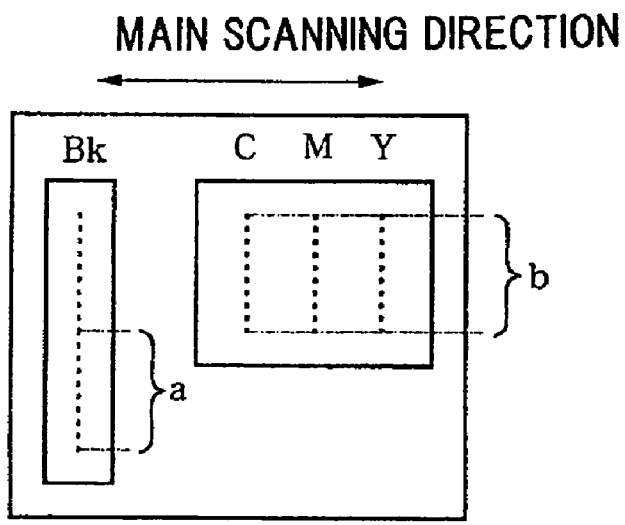
FIG. 9 is a view showing an example of a recording head used in the present invention.

FIG. 9 shows another example of a recording head that can be used in the present invention. In FIG. 9, as in the case of FIG. 8, an image having the black image and the color image mixed therein is formed by using a part a of an ejection orifice line for a black ink, for the black ink, and a part b which is the whole ejection orifice line for a color ink, for the color inks of C, M and Y, similarly to the above described case.

Figure 10:
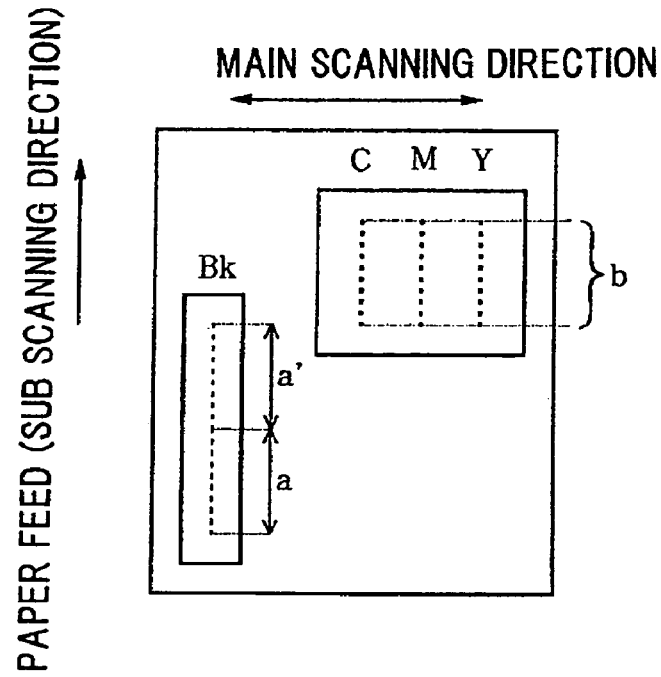
FIG. 10 is a view showing an example of a recording head used in the present invention.

FIG. 10 shows another example of a recording head that can be used in the present invention. In FIG. 10, as in the case of FIG. 8, an image having the black image and the color image mixed therein is formed by using a part a of an ejection orifice line for a black ink, for the black ink, and a part b which is the whole ejection orifice line for a color inks for the color inks of C, M and Y. Here, in the recording head shown in FIG. 10, the part b of the ejection orifice line for the color ink is placed so as to be separated from the part a of the ejection orifice line for the black ink, by a distance of an one-paper feed length a'. As a result, the recording head having the above described structure forms the color image further after a period of one circuit scanning after the black image has been formed. Accordingly, the recording head shown in FIG. 10 has a more advantageous structure in preventing bleeding between the black image and the color image, than the recording head shown in FIG. 9 has.

Figure 11:
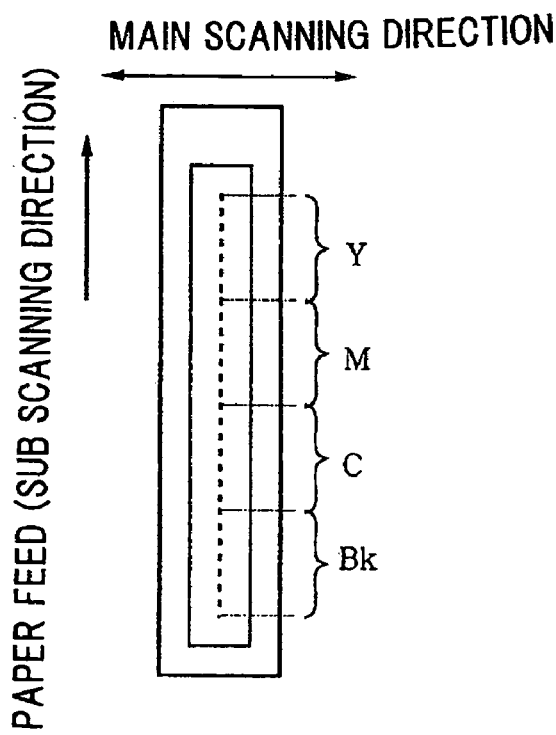
FIG. 11 is a view showing an example of a recording head used in the present invention.

FIG. 11 shows another example of a recording head that can be used in the present invention. A recording head shown in FIG. 11 has an ejection orifice line for a black ink and an ejection orifice line for a color ink placed in a single row sequentially in a sub-scanning direction, and accordingly when recording, forms a color image after forming a black image in accordance with paper feed.

Figure 12:
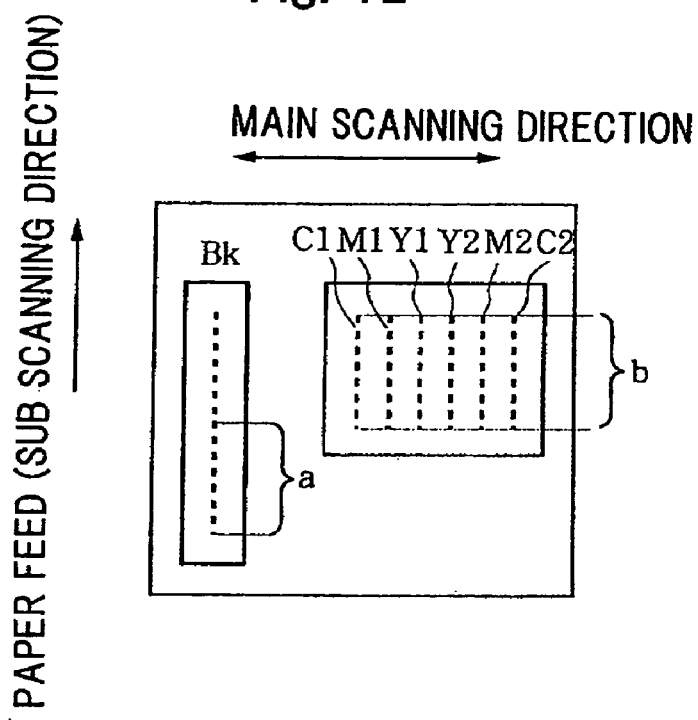
FIG. 12 is a view showing an example of a recording head used in the present invention.

FIG. 12 shows another example of a recording head that can be used in the present invention. The recording head shown in FIG. 12 has two ejection orifice lines for each color ink of cyan ink (C1, C2), magenta ink (M1, M2) and yellow ink (Y1, Y2) installed symmetrically in a main-scanning direction, so that the recording order of the color inks can be equal in the forward direction and backward direction of the main-scanning direction. As a result, the recording head can print data in both ways, when forming an image having a black image and a color image mixed therein. In this case, at first, the black image is formed by using a part a of an ejection orifice line for the black ink; subsequently, a recording medium is carried only by a distance a in a sub-scanning direction; a recording head returns in a main-scanning direction for the next recording; and in the returning process, the color image is formed in an image region previously formed by the part a of the ejection orifice line for the black ink on the recording medium, in one-pass recording, by using a part b of an ejection orifice line for color inks. In the returning process, the part a of the ejection orifice line for the black ink forms the image in the next region. Through the repetition of the operation, the image having the black image and the color image mixed therein is formed.

The recording head which can print data in both ways as shown in FIG. 12 can be modified into a more advantageous structure similar to that of the recording he ad described in FIG. 10, so as to inhibit bleeding between the black image and the color image, by arranging the part b of the ejection orifice line for the color ink so as to be separated from the part a of the ejection orifice line for the black ink, by a distance of an one-paper feed length a' (cf. FIG. 13), and thereby arranging a time difference of one circuit scanning between the formation of the black image and the formation of the color image.

Up to this point, an image forming method according to the present invention was described. As a matter of course, a form of a recording head that can be used in the image forming method according to the present invention is not limited to FIGS. 8 to 13. In addition, the number of passes depends on a recording device, so that the form of a recording head is not limited to one-pass recording.

When forming an image having a black part and a color part mixed therein on plain paper by using ink, if the ink employs an aqueous ink according to the present invention as a black ink, a coloring material composing the black ink on the paper is considered to progress agglomeration or dispersion destruction comparatively faster than the other inks do, as described above. The image forming method according to the present invention can form the image with little bleeding by using an aqueous ink according to the present invention as a black ink, forming the image of the color ink after forming the image of the black ink, and more preferably by scanning a recording head to apply the color ink onto a medium after an interval of at least one scanning period after the recording head for applying the black ink has finished scanning, because thereby even when the color ink contacts with the black ink, both the inks do not cause color mixture bleeding between both the inks existing on paper. Specifically, the image forming method provides the above described superior effect only by arranging a time difference between image formation with black ink and image formation with each color ink of color inks, without needing a method of requiring the upsizing of a device such as a method of multipass recording which completes recording by a plural time of scanning and accordingly requires a long recording period of time, and a method of preparing recovering systems independently for a black ink and a color ink.

(Ink Jet Recording Method, Ink Cartridge, Recording Unit and Ink Jet Recording Apparatus)

Figure 2:
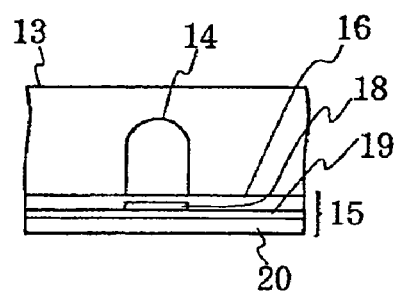
FIG. 2 is a side view in a longitudinal direction of the head of the ink jet recording apparatus.

In the next place, an example of an ink jet recording apparatus suitable for the present invention will be described below. At first, one example of a structure for a recording head that is a main part of the ink jet recording apparatus using thermal energy is shown in FIGS. 1 and 2. FIG. 1 is a cross sectional view of the recording head 13 along an ink channel, and FIG. 2 is a side view of a cut surface by a line A-B in FIG. 1. The recording head 13 is obtained by adhesively bonding a glass, ceramic, silicon or plastic plate having the channel (nozzle) 14 for passing ink with a heating element substrate member 15.

The heating element substrate member 15 is composed of a protective layer 16 formed of silicon oxide, silicon nitride and silicon carbide or the like; electrodes 17-1 and 17-2 formed of aluminum, gold and an aluminum-copper alloy or the like; a heating resistor layer 18 formed of a refractory material such as $HfB_2$, TaN and TaAl; a heat storage layer 19 for med of thermally oxidized silicon and aluminum oxide or the like; and a substrate 20 formed of a material with an adequate heat dissipation characteristics, such as silicon, aluminum and aluminum nitride.

Upon application of pulse wise electric signals to the electrodes 17-1 and 17-2 of the recording head 13, heat is abruptly generated at the region denoted by n in the heating resistor substrate member 15, so that bubbles are generated in ink 21 coming into contact with the surface of this region. The pressure thus produced thrusts out a meniscus 23 and the ink 21 is ejected through the nozzle 14 from an ejection orifice 22 in the form of a minute ink drop 24 to fly toward a recording medium 25.

Figure 3:
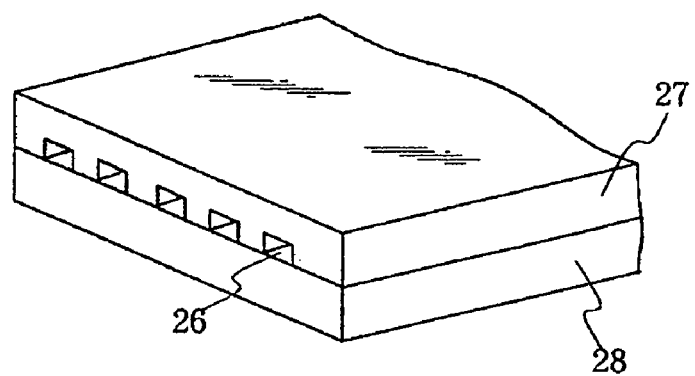
FIG. 3 is an external perspective view of a multi-head obtained from the head as shown in FIG. 1.

FIG. 3 shows an external perspective view of one example of a multi-head which arrays many recording heads shown in FIG. 1 therein. The multi-head is made by adhesively bonding a glass plate 27 having a multi-nozzle 26, with a heating head 28 which is similar to the heating element substrate member described with reference to FIG. 1.

Figure 4:
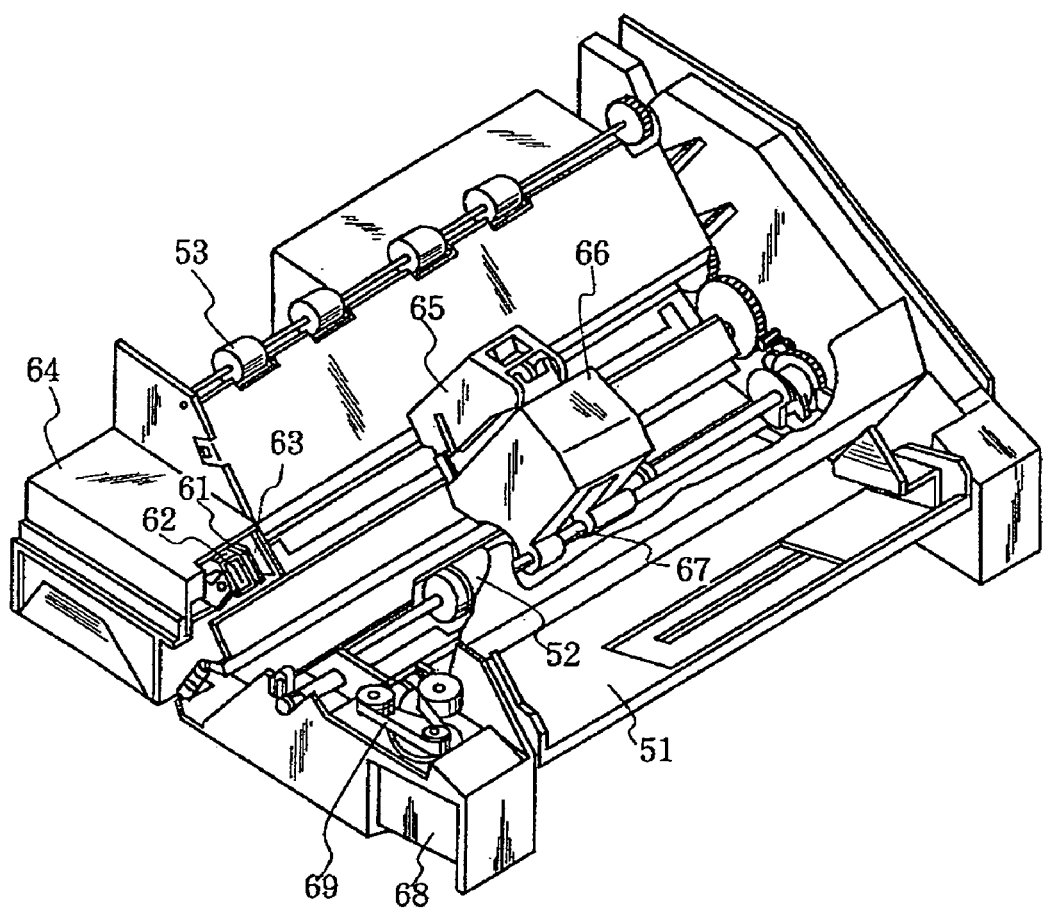
FIG. 4 is a perspective view showing an example of an ink jet recording apparatus.

FIG. 4 shows one example of an ink jet recording apparatus mounting the head therein. In FIG. 4, reference numeral 61 denotes a blade of a wiping member, and the one end is fixed with a blade-holding member, so that the blade has a form of a cantilever. The blade 61 is arranged in a position adjacent to a recording region to be recorded by a recording head 65, and is held in a projecting form into a moving path of the recording head 65, in the case of an illustrated example.

Reference numeral 62 denotes a cap of a projecting opening face of the recording head 65, which is arranged at a home position adjacent to the blade 61, and has a structure of moving in a direction perpendicular to a moving direction of the recording head 65, abutting with an ink ejection orifice face and capping it. Furthermore, reference numeral 63 denotes an ink absorber arranged adjacently to the blade 61, and is held in a projecting form into the moving path of the recording head 65, similarly to the blade 61. An ejection recovery part 64 is composed of the above described blade 61, the cap 62 and the ink absorber 63, and the blade 61 and the ink absorber 63 remove moisture and dust around the ejection orifice face.

Reference numeral 65 denotes a recording head that has an eject energy production means, ejects ink to a recording medium facing the ejection orifice face provided with an ejection orifice and records data. Reference numeral 66 denotes a carriage which mounts the recording head 65 thereon and moves the recording head 65. The carriage 66 is slidably engaged with a guide shaft 67, and one part of the carriage 66 is connected (not shown) with a belt 69 that is driven by a motor 68. Thereby, the carriage 66 can move along the guide shaft 67, and can move the recording head 65 to the recording region and the adjacent region.

Reference numeral 51 denotes a paper feeding part for inserting a recording medium, and reference numeral 52 denotes a paper feeding roller driven by an unshown motor. The above structure feeds a recording medium to a position facing to the ejection orifice face of the recording head 65, and delivers the paper to a delivery part provided with a delivery roller 53, along with the progression of recording. In the above described structure, when the recording head 65 returns to the home position after having finished recording, the cap 62 of the ejection recovery part 64 withdraws from the moving path of the recording head 65, but the blade 61 projects into the moving path. As a result, the ejection orifice of the recording head 65 is wiped.

By the way, when the cap 62 abuts the eject surface of the recording head 65 to cap it, the cap 62 moves so as to project into the moving path of the recording head. When the recording head 65 moves from the home position to a recording start position, the cap 62 and the blade 61 stay in the same position as in the above described wiping. As a result, the ejection orifice face of the recording head 65 is wiped also when the recording head 65 moves on the above way. The recording head moves to the home position not only when having finished recording and recovering eject as described above, but also moves to the home position adjacent to the recording region at a predetermined interval, while the recording head moves over the recording region for the purpose of recording, and is wiped along with the movement.

Figure 5:
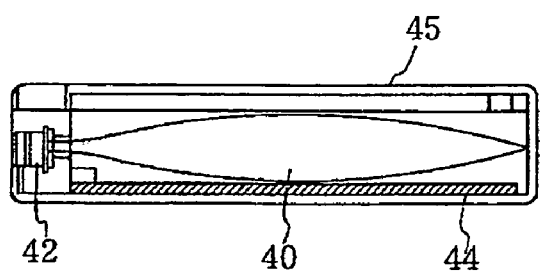
FIG. 5 is a cross sectional view in a longitudinal direction of an ink cartridge.

FIG. 5 is a view showing one example of an ink cartridge for containing an ink which is supplied to a recording head through an ink feeding member, for instance, a tube. In the figure, reference numeral 40 denotes an ink containing portion for containing the ink to be supplied, for instance, an ink bag, and reference numeral 42 is a stopper made of rubber, which is installed at the nose. In the stopper 42, a needle (not shown) is inserted to enable the ink in the ink bag 40 to be supplied to the head. Reference numeral 44 denotes an ink absorber for containing wasted ink. The ink containing portion has a contacting sur face with the ink, preferably made of a polyolefin, particularly polyethylene.

Figure 6:
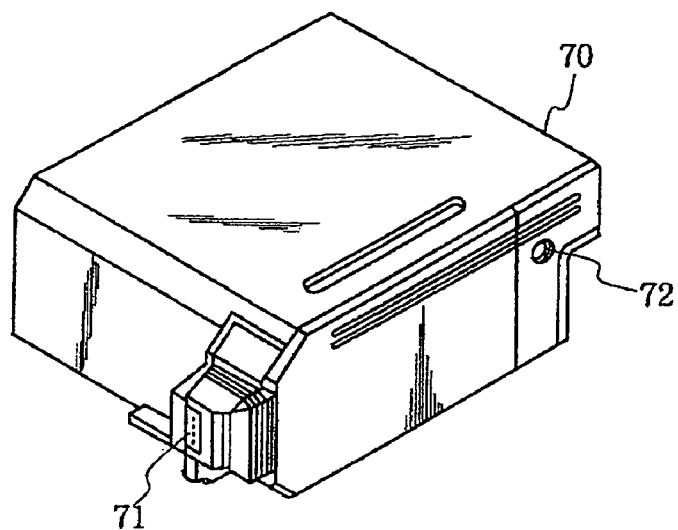
FIG. 6 is a perspective view showing an example of a recording unit.

An ink jet recording apparatus preferably used in the present invention includes not only a device having a separated head from an ink cartridge as described above, but also a device having them integrated as shown in FIG. 6. In FIG. 6, reference numeral 70 denotes a recording unit having a structure containing an ink containing portion for containing ink, for instance, an ink absorber, and a head 71 having a plurality of orifices for ejecting the ink stored in the ink absorber, in the form of ink drops. It is preferable to use polyurethane for a material of the ink absorber. Alternatively, the ink containing portion may have a structure such as an ink bag containing a spring therein, instead of the ink absorber. Reference numeral 72 denotes an air-communicating opening for communicating the inside of the cartridge with air. The recording unit 70 is used in place of the recording head 65 shown in FIG. 4, and is removable from a carriage 66.

Figure 7:
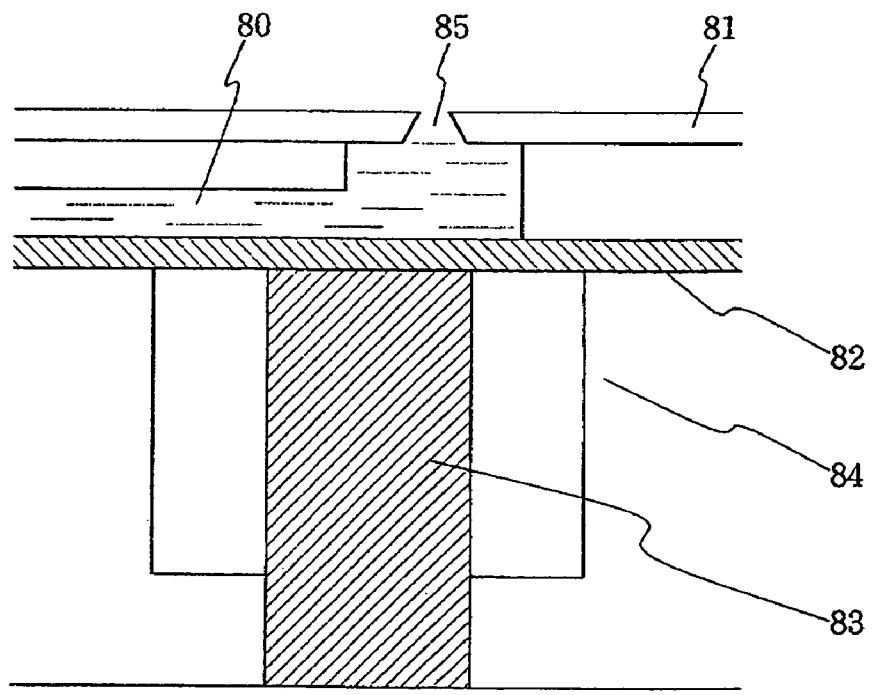
FIG. 7 his a view showing an example of a configuration of a recording head.

In the next place, a preferred example of an ink jet recording apparatus using mechanical energy will be described. The ink jet recording apparatus using mechanical energy includes an on-demand ink jet recording head which has a nozzle-forming substrate with a plurality of nozzles, a pressure-generating element which is arranged to face the nozzles and is made of a piezoelectric material and an electro conductive material, and ink which fills the perimeter of the pressure generating element, displaces the pressure generating element by an applied voltage, and ejects a small droplet of ink from the nozzle. FIG. 7 shows one example of a structure of the recording head that is a main part of the recording device.

The recording head is composed of an ink channel 80 communicating with an ink chamber (not shown); an orifice plate 81 for ejecting an ink drop of a desired volume; a diaphragm 82 for directly exerting pressure on the ink; a piezoelectric device 83 which is connected to the diaphragm 82 and is displaced by an electric signal; and a substrate 84 for supporting and fixing the orifice plate 81, the diaphragm the 82 and the like.

In FIG. 7, the ink channel 80 is formed of a photosensitive resin; the orifice plate 81 has an ejection orifice 85 formed by drilling a metal such as stainless and nickel through electroforming or press working; the diaphragm 82 is formed of a film of a metal such as stainless steel, nickel and titanium and a highly elastic resin film; and the piezoelectric device 83 is formed of a dielectric material such as barium titanate and PZT. The recording head having the above described structure works to record data by applying pulsed voltage to the piezoelectric device 83 to generate distortion stress; deforming the diaphragm connected to the piezoelectric device 83 through the energy; perpendicularly pressurizing an ink in the ink channel 80; and ejecting an ink drop (not shown) from an ejection orifice 85 of the orifice plate 81. The recording head having the above described structure is used after having been incorporated in an ink jet record device similar to the device shown in FIG. 4. The detailed operation of the ink jet recording apparatus may be similar to the above described one.

EXAMPLES

Next, the present invention will be described in more detail by way of examples, comparative examples and reference examples. The present invention is not limited to the following examples as long as they are within its scope. Hereafter, "part(s)" and "%" are based on mass unless otherwise specified.

(Preparation of Pigment-Dispersion Solutions)
(Preparation of Pigment-Dispersion Solution A)

1.5 g of 4-amino-1,2-benzene dicarboxylic acid was added at 5° C. to a solution of 5 g of concentrated hydrochloric acid dissolved in 5.5 g of water. This solution was stirred in an ice bath to be always maintained at 10° C. or less and a solution of 1.8 g of sodium nitrite dissolved in 9 g of 5° C. water was added to this solution. After the resulting solution was further stirred for 15 minutes, 6 g of carbon black having a specific surface area of 220 $m^2$/g and a DBP oil absorption of 105 mL/100 g was added and mixed. Thereafter, the solution was stirred for another 15 minutes. The obtained slurry was filtered with a paper filter (trade name Standard Filter Paper No. 2, made by Advantec Co., Ltd.), and pigment particles were thoroughly washed with water and dried in an oven heated at 110° C. to prepare self-dispersion carbon black A. Further, water was added to the obtained self-dispersion carbon black A to prepare a dispersion solution having a pigment concentration of 10 mass %. With the above process, a pigment-dispersion solution A in which the self-dispersion carbon black A having —C$_6$H$_3$—(COONa)$_2$ group introduced to the surface of carbon black particle was dispersed in water was obtained.

The ionic group density of the prepared self-dispersion carbon black A was measured, and it was 3.1 μmol/m$^2$. In the measurement of the ionic group density, ion meter (made by DKK-Toa Corporation) was used to measure the sodium ion concentration in the above pigment dispersion solution A, and the obtained result was converted into the ionic group density of the self-dispersion carbon black A.

(Preparation of Pigment-Dispersion Solution B)

A self-dispersion carbon black B was prepared by substituting an ammonium ion for a sodium ion in a pigment-dispersion solution A obtained above, with an ion exchange method. Further, water was added to the obtained self-dispersion carbon black B to prepare a dispersion solution having a pigment concentration of 10 mass %. With the above process, a pigment-dispersion solution B in which the self-dispersion carbon black B having —C$_6$H$_3$—(COONH$_4$)$_2$ group introduced to the surface of carbon black particle was dispersed in water was obtained.

The ionic group density of the prepared self-dispersion carbon black B was 3.1 μmol/m$^2$.

(Preparation of Pigment-Dispersion Solution C)

1.55 g of p-aminobenzoic acid was added at 5° C. to a solution of 5 g of concentrated hydrochloric acid dissolved in 5.5 g of water. This solution was stirred in an ice bath to be always maintained at 10° C. or less and a solution of 1.8 g of sodium nitrite dissolved in 9 g of 5° C. water and was added to this solution. After the resulting solution was further stirred for 15 minutes, 6 g of carbon black having a specific surface area of 220 m$^2$/g and a DBP oil absorption of 105 mL/100 g was added and mixed. Thereafter, the solution was stirred for another 15 minutes. The obtained slurry was filtered with a paper filter (trade name: Standard Filter Paper No. 2, made by Advantec Co., Ltd.), and pigment particles were thoroughly washed with water and dried in an oven heated at 110° C. to prepare self-dispersion carbon black C. Further, water was added to the obtained self-dispersion carbon black C to prepare a dispersion solution having a pigment concentration of mass %. With the above process, a pigment-dispersion solution C in which the self-dispersion carbon black C having —C$_6$H$_4$—COONa group introduced to the surface of a carbon black particle was dispersed in the water was obtained.

The ionic group density of the prepared self-dispersion carbon black C was measured in the same manner as that of self-dispersion carbon black A and it was 2.6 μmol/m$^2$.

(Preparation of Pigment-Dispersion Solution D)

A self-dispersion carbon black D was prepared by substituting an ammonium ion for a sodium ion in a pigment-dispersion solution C obtained above, with an ion exchange method. Further, water was added to the obtained self-dispersion carbon black D to prepare a dispersion solution having a pigment concentration of 10 mass %. With the above process, a pigment-dispersion solution D in which the self-dispersion carbon black D having —C$_6$H$_4$—COONH$_4$ group introduced to the surface of carbon black particle was dispersed in water was obtained.

The ionic group density of the prepared self-dispersion carbon black D was 2.6 μmol/m$^2$.

(Preparation of Inks)

Inks for Examples 1 to 8 and Reference Examples 1 to 3 were prepared by mixing components described in the following Table 1, sufficiently stirring them to dissolve or disperse them, and then followed by pressure filtration with a microfilter of 3.0 μm in pore size (made by Fuji Photo Film Co., Ltd.).

TABLE 1

|  | Example | | | | | | | | Reference Example | | |
| --- | --- | --- | --- | --- | --- | --- | --- | --- | --- | --- | --- |
|  | 1 | 2 | 3 | 4 | 5 | 6 | 7 | 8 | 1 | 2 | 3 |
| Pigment-dispersion solution A | 35.00 | 35.00 | | | | | | | | | |
| Pigment-dispersion solution B | | | 35.00 | 35.00 | 35.00 | 35.00 | 35.00 | 35.00 | | | |
| Pigment-dispersion solution C | | | | | | | | | 35.00 | 35.00 | |
| Pigment-dispersion solution D | | | | | | | | | | | 35.00 |
| Glycerin | 6.00 | 6.00 | 6.00 | 6.00 | 6.00 | 6.00 | 6.00 | 6.00 | 6.00 | 6.00 | 6.00 |
| Diethyleneglycol | 5.00 | 5.00 | 5.00 | 5.00 | 5.00 | 5.00 | 5.00 | 5.00 | 5.00 | 5.00 | 5.00 |
| 2-pyrrolidone | 5.00 | 5.00 | 5.00 | 5.00 | 5.00 | 5.00 | 5.00 | 5.00 | 5.00 | 5.00 | 5.00 |
| Trimethylolpropane | 4.00 | 4.00 | 4.00 | 4.00 | 4.00 | 4.00 | 4.00 | 4.00 | 4.00 | 4.00 | 4.00 |
| Acetylenol E-100(*) | 0.15 | 0.15 | 0.15 | 0.15 | 0.15 | 0.15 | 0.15 | 0.15 | 0.15 | 0.15 | 0.15 |
| Sodium benzoate | 0.72 | | | | | | | | 0.72 | | |
| Ammonium benzoate | | 0.70 | 0.70 | | | | | | | 0.70 | 0.70 |
| Ammonium acetate | | | | 0.39 | | | | | | | |
| Ammonium nitrate | | | | | 0.40 | | | | | | |
| Diammonium succinate | | | | | | 0.38 | | | | | |
| Diammonium phthalate | | | | | | | 0.50 | | | | |
| Ammonium sulfate | | | | | | | | 0.33 | | | |
| Pure water | 44.13 | 44.15 | 44.15 | 44.46 | 44.45 | 44.47 | 44.35 | 44.52 | 44.13 | 44.15 | 44.15 |

(*)Acetyleneglycol ethylene oxide adduct (made by Kawaken Fine Chemicals Co., Ltd.)

(Evaluation)

The inks obtained with the above described method were subjected to the following evaluations.

A recorded matter for the evaluations was produced by using a modified ink jet recording apparatus BJS700 (made by Canon Inc.) having an on-demand multi-recording head which ejects ink by applying thermal energy to the ink in response to a recording signal. A default mode was selected in the printer driver. Control settings of the default mode are described below.

Type of paper: plain paper
Print quality: standard
Color adjustment: automatic (Print Density)

Each ink of Examples 1 to 8 and Reference Examples 1 to 3 was used for preparing a recorded matter having characters including a solid image area of 2 cm×2 cm printed on the following five types of recording media, by using the ink jet recording apparatus in which a eject amount per dot of ink is set within 30 ng±10%. The recorded matter was reserved for one day and then was subjected to the measurement for the print density of the solid image area. The print density was measured with the use of a reflection density meter (trade name: Macbeth RD-918 made by Macbeth).

PPC paper office planner (made by Canon Inc.)
PPC paper GF-500 (made by Canon Inc.).
PPC paper 4024 (made by Xerox)
PPC paper prober bond (made by Fox River)
PPC paper (made by Neusiedler) for Canon Inc.

An evaluation criterion for print density is described below. Evaluation results are shown in Table 2.

A: An average value of print densities measured on five recording media is 1.45 or more.

B: An average value of print densities measured on five recording media is 1.40 or more and less than 1.45.

C: An average value of print densities measured on five recording media is less than 1.40.

(Character Quality)

Each ink of Examples 1 to 8 and Reference Examples 1 to 3 was used for preparing a recorded matter having characters with a plurality of font sizes printed thereon, and a degree of the feathering of the characters on the recorded matter was examined through visual inspection. The recorded matter was prepared on an office planner (made by Canon Inc.). An evaluation criterion for character quality is described below. Evaluation results are shown in Table 2.

A: The feathering of characters is almost unnoticeable.

B: The feathering of characters is noticeable, but in a level of practically causing no problem.

C: The feathering of characters is remarkable.

(Bleeding Resistance)

Before evaluating bleeding resistance, color inks (three colors of cyan, magenta and yellow) were prepared. Each color ink was prepared by mixing each component described below, sufficiently stirring the resultant liquid, and then followed by pressure filtration with a microfilter of 0.2 μm in pore size (made by Fuji Photo Film Co., Ltd.). In addition, in the composition of the following color ink, acetylenol E-100 (made by Kawaken Fine Chemicals Co., Ltd.) is an acetylene-alcohol-based surfactant shown in the previously described structural formula (2).

| (Cyan ink) | |
|---|---|
| DBL (direct blue) 199: | 3.5 parts |
| Glycerin: | 7.5 parts |
| Diethyleneglycol: | 7.5 parts |
| Acetylenol E-100: | 1.0 part |
| Pure water: | 80.5 parts |
| (Magenta ink) | |
| AR (acid red) 289: | 2.5 parts |
| Glycerin: | 7.5 parts |
| Diethylene glycol: | 7.5 parts |
| Acetylenol E-100: | 1.0 part |
| Pure water: | 81.5 parts |
| (Yellow ink) | |
| DY (direct yellow) 86: | 2.5 parts |
| Glycerin: | 7.5 parts |
| Diethylene glycol: | 7.5 parts |
| Acetylenol E-100: | 1.0 part |
| Pure water: | 81.5 parts |

Figure 13:
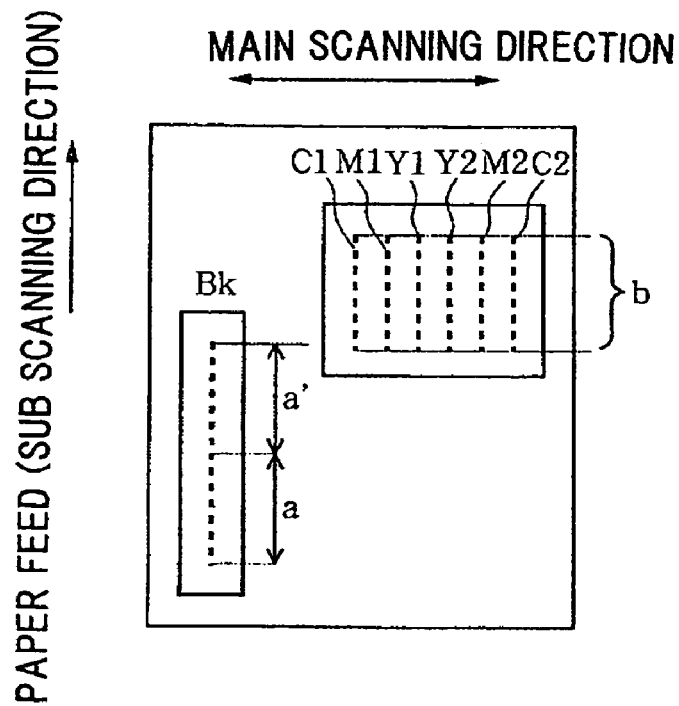
FIG. 13 is a view showing an example of a recording head used in the present invention.

Each black ink of Examples 1 to 8 and Reference Examples 1 to 3 and the color inks obtained with the above described method and an ink jet recording apparatus which has been modified so as to have a recording head with a structure shown in FIGS. 12 and 13 were used for preparing a recorded matter in which images were so printed that solid areas of black and each color (yellow, magenta and cyan) were adjacent to each other. A degree of bleeding in a boundary between black ink and each color ink on the obtained recorded matter was visually inspected. The recorded matter was prepared on an office planner (made by Canon Inc.). An evaluation criterion for bleeding resistance is described below. Evaluation results are shown in Table 2.

AA: Bleeding is not visible.

A: Bleeding is almost unnoticeable.

B: Bleeding is noticeable, but in a level of practically causing no problem.

C: Bleeding is so remarkable that the boundary between colors is not clear.

TABLE 2

| | Head structure | Example | | | | | | | | Reference Example | | |
|---|---|---|---|---|---|---|---|---|---|---|---|---|
| | | 1 | 2 | 3 | 4 | 5 | 6 | 7 | 8 | 1 | 2 | 3 |
| Print density | — | A | A | A | A | A | A | A | A | B | B | B |
| Character quality | — | A | A | A | A | A | A | A | A | A | A | A |
| Bleeding resistance | FIG. 12 | A | A | A | A | A | A | A | A | B | B | B |
| | FIG. 13 | AA | AA | AA | AA | AA | AA | AA | AA | A | A | A |

From Table 2, it is understood that recorded matters printed by using the inks of Examples 1 to 8 clearly show improved print density and bleeding resistance in comparison with those by using the inks of Reference Examples 1 to 3. It is also understood that recorded matters printed by using a recording head having a structure shown in FIG. 13 show a adequate bleeding resistance in all Examples compared to those by using a recording head having a structure shown in FIG. 12. It is also understood that Examples 1 to 8 and Reference Examples 1 to 3 have no problem with a level of character quality.

(Water Resistance)

Each ink in Examples 1 to 8 was used to prepare a recorded matter having characters including a solid image area printed thereon. The recorded matter was left for a predetermined period of time after recording, then the printed part was exposed to running water, and the state of scumming was evaluated through visual inspection. In preparing the recorded matter, the following five sorts of recording media were used.

PPC paper office planner (made by Canon Inc.)
PPC paper GF-500 (made by Canon Inc.)
PPC paper 4024 (made by Xerox)
PPC paper prober bond (made by Fox River)
PPC paper (made by Neusiedler) for Canon Inc.

An evaluation criterion for water resistance is described below. Evaluation results are shown in Table 3.

AA: Scumming on all five recording media becomes unnoticeable within one hour after recording.

A: Scumming on all five recording media becomes unnoticeable within one day after recording.

B: Some paper still shows remarkable scumming even after one day or longer has elapsed after recording.

(Dispersion Stability: Dispersion Stability of Pigment when Water Vaporizes)

Each ink of Examples 1 to 8 was charged in an open vessel, was heated at 60° C. to evaporate water and the like, and was concentrated into a fixed amount, for instance, into 60% of initial mass. This was conducted for the purpose of showing that ink according to the present invention has superior dispersion stability, by evaluating the dispersion stability of the ink in a stricter condition. The dispersion stability of a pigment when water vaporizes was evaluated on the basis of the viscosity of the concentrated ink and a formed degree of pigment agglomerate. An evaluation criterion for the dispersion stability of pigment when water vaporizes is described below. Evaluation results are shown in Table 3.

AA: The viscosity of ink varies little and the pigment in the ink agglomerates little before and after the ink is left.

A: The viscosity of ink varies a little and the pigment in the ink agglomerates a little before and after the ink is left, but in a level of practically causing no problem.

B: The viscosity of ink greatly varies or the pigment in the ink agglomerates before and after the ink is left.

TABLE 3

| | Example | | | | | | | |
|---|---|---|---|---|---|---|---|---|
| | 1 | 2 | 3 | 4 | 5 | 6 | 7 | 8 |
| Water resistance | B | A | A | A | AA | AA | AA | AA |
| Dispersion stability | B | B | B | B | B | A | AA | AA |

From Table 3, it is understood that recorded matters printed by using inks of Examples 2 to 8 show water resistance in a level of practically causing no problem. The recorded matters printed particularly by using inks of Examples 5 to 8 among the above examples shows adequate water resistance in a comparatively short period of time after recording. It is also understood that the pigments in the inks of Examples 6 to 8 have dispersion stability in a level of practically causing no problem when water vaporizes. The pigments particularly in the inks of Examples 7 and 8 among the above examples show superior dispersion stability when water vaporizes.

This application claims priority form Japanese Patent Application No. 2004-248228 filed on Aug. 27, 2004, which is hereby incorporated by reference herein.

What is claimed is:

1. An aqueous ink comprising a self-dispersion pigment and a salt, wherein the self-dispersion pigment is a pigment containing a pigment particle having a —R—$(COOM_1)_n$ group bonded to a surface of the pigment particle, wherein R represents an alkylene group or an aromatic ring; $M_1$ represents a hydrogen atom, an alkali metal, an ammonium or an organic ammonium; and n is an integer of 2 or more.

2. The aqueous ink according to claim 1, wherein in the —R—, a carbon atom adjacent to the carbon atom bound to —$(COOM_1)$ is also bound to —$(COOM_1)$.

3. The aqueous ink according to claim 1, wherein n is 2.

4. The aqueous ink according to claim 1, wherein the R is $C_6H_3$.

5. The aqueous ink according to claim 1, wherein the $M_1$ is ammonium.

6. The aqueous ink according to claim 1, wherein the salt is at least one selected from the group consisting of $(M_2)NO_3$, $CH_3COO(M_2)$, $C_6H_5COO(M_2)$, $C_2H_4(COO(M_2))_2$, $C_6H_4COO(M_2)_2$ and $(M_2)_2SO_4$, where in $M_2$ represents an a ammonium or an organic ammonium.

7. The aqueous ink according to claim 6, wherein the $M_2$ is an ammonium.

8. The aqueous ink according to claim 1, wherein the salt is at least one selected from the group consisting of $NH_4NO_3$, $C_2H_4(COONH_4)_2$, $C_6H_4(COONH_4)_2$ and $(NH_4)_2SO_4$.

9. The aqueous ink according to claim 1, wherein the salt is at least one selected from the group consisting of $C_2H_4(COO(M_2))_2$, $C_6H_4(COO(M_2))_2$ and $(M_2)_2SO_4$.

10. The aqueous ink according to claim 1, wherein the aqueous ink is used for ink jet recording.

11. An ink jet recording method comprising a step of ejecting an ink by an ink jet method, wherein the ink is the aqueous ink according to claim 1.

12. An ink cartridge comprising an ink-containing portion for containing an ink, wherein the ink is the aqueous ink according to claim 1.

13. A recording unit comprising an ink-containing portion for containing an ink and a recording head for ejecting an ink therefrom, wherein the ink is the aqueous ink according to claim 1.

14. An ink jet recording apparatus comprising an ink-containing portion for containing an ink and a recording head for ejecting an ink therefrom, wherein the ink is the aqueous ink according to claim 1.

15. An image forming method for performing recording on plain paper by an ink jet recording method by using a black ink and at least one color ink, wherein the aqueous ink according to claim 1 is used as the black ink, and wherein in forming an image composed of an image formed by the black ink and an image formed by the color ink are adjacent to each other, performing scanning for applying the black to form the image and thereafter performing scanning for applying the color ink to the area where the image has been formed by the precedent scanning.

16. The image forming method according to claim 15, wherein the color ink is applied by scanning with delay of at least one scanning after application of the black ink by scanning.

17. The image forming method according to claim 15, wherein the inks are applied by use of a recording head in which an ejection orifice line for ejecting a black ink therefrom and an ejection orifice line for ejecting a color ink are placed to be shifted from each other in a sub-scanning direction.

18. An aqueous ink comprising a self-dispersion pigment and $M_1^+$, wherein the self-dispersion pigment is a pigment containing a pigment particle having a —R—$(COO^-)_n$ group bonded to a surface of the pigment particle, wherein R represents an alkylene group or an aromatic ring; and n is an integer of 2 or larger, and wherein $M_1$ represents a hydrogen atom, an alkali metal, an ammonium or an organic ammonium, and wherein the aqueous ink further comprises at least one group selected from the group consisting of $NO_3^-$, $CH_3COO^-$, $C_6H_5COO^-$, $C_2H_4(COO^-)_2$, $C_6H_4(COO^-)_2$ and $SO_4^{2-}$, and $M_2^+$, wherein $M_2$ represents an alkali metal, an ammonium or an organic ammonium.

19. The aqueous ink according to claim 9, wherein the $M_2$ is an ammonium.

20. The aqueous ink according to claim 1, wherein the salt is $C_6H_4(COO(M_2))_2$ or $(M_2)_2SO_4$.

21. The aqueous ink according to claim 20, wherein the $M_2$ is an ammonium.

* * * * *

UNITED STATES PATENT AND TRADEMARK OFFICE
CERTIFICATE OF CORRECTION

PATENT NO. : 7,267,717 B2
APPLICATION NO. : 11/356108
DATED : September 11, 2007
INVENTOR(S) : Tomonari Watanabe et al.

It is certified that error appears in the above-identified patent and that said Letters Patent is hereby corrected as shown below:

ON THE TITLE PAGE

In Item (75), Inventors,

"Masashi Ogasawara, Tokyo" should read --Masashi Ogasawara, Machida--.

COLUMN 1
Line 28, "resent" should read --recent--.

COLUMN 4
Line 3, "cross sectional" should read --cross-sectional--.
Line 11, "across sectional" should read --a cross-sectional--.

COLUMN 6
Line 53, "a H type" should read --an H type--.

COLUMN 7
Line 18, "Black; FW200" should read --Black FW200--.
Line 28, "abut" should read --but--.
Line 61, "followings" should read --following--.

COLUMN 8
Line 4, "violet" should read --violet:--.

COLUMN 10
Line 57, "followings" should read --following--.

COLUMN 11
Line 59, "base-dissolved" should read --base dissolved--.

COLUMN 12
Line 2, "includes" should read --include--.

COLUMN 13
Line 18, "$1.5(ml/m^2/msec^{1/2})$ should read --$1.5(ml/m^2/msec^{1/2})$.--.

UNITED STATES PATENT AND TRADEMARK OFFICE
CERTIFICATE OF CORRECTION

PATENT NO. : 7,267,717 B2
APPLICATION NO. : 11/356108
DATED : September 11, 2007
INVENTOR(S) : Tomonari Watanabe et al.

It is certified that error appears in the above-identified patent and that said Letters Patent is hereby corrected as shown below:

COLUMN 14
Line 24, "a" should read --an--.
Line 45, "inks" should read --ink,--.
Line 50, "an one-paper" should read --a one-paper--.

COLUMN 15
Line 22, "he ad" should read --head--.
Line 27, "an one-paper" should read --a one-paper--.

COLUMN 16
Line 4, "cross sectional" should read --cross-sectional--.
Line 16, "for med" should read --formed--.
Line 17, "with an" should read --with--.

COLUMN 17
Line 42, "sur face" should read --surface--.

COLUMN 18
Line 16, "the 82" should read --82--.
Line 19, "stainless" should read --stainless steel--.

COLUMN 23
Line 7, "a" should be deleted.

UNITED STATES PATENT AND TRADEMARK OFFICE
CERTIFICATE OF CORRECTION

PATENT NO. : 7,267,717 B2
APPLICATION NO. : 11/356108
DATED : September 11, 2007
INVENTOR(S) : Tomonari Watanabe et al.

It is certified that error appears in the above-identified patent and that said Letters Patent is hereby corrected as shown below:

COLUMN 24
Line 5, "shows" should read --show--.
Line 20, "wherein" should read --¶ wherein--.
Line 39, "$C_6H_4COO(M_2)_2$," should read --$C_6H_4(COO(M_2))_2$--.

Signed and Sealed this

Thirteenth Day of May, 2008

JON W. DUDAS
*Director of the United States Patent and Trademark Office*